United States Patent [19]
Jackson

[11] 4,141,086
[45] Feb. 27, 1979

[54] FOG FREE SKI MASK

[76] Inventor: Allen F. Jackson, P.O. Box 1271, Breckenridge, Colo. 80424

[21] Appl. No.: 778,600

[22] Filed: Mar. 17, 1977

[51] Int. Cl.² ............................................. A61F 9/02
[52] U.S. Cl. ...................................................... 2/436
[58] Field of Search .................... 2/2.1 R, 2.1 A, 463, 2/6, 7, 427, 428, 431, 435, 436, 84, 173, 202; 128/141 R, 142, 142.7, 145 R

[56] References Cited
U.S. PATENT DOCUMENTS

| | | |
|---|---|---|
| 276,699 | 5/1883 | McIntosh ................................. 2/5 |
| 1,113,675 | 10/1914 | Morgan ............................. 128/142.7 |
| 1,263,593 | 4/1918 | Nordstrom et al. ............. 128/145 R |
| 2,314,889 | 3/1943 | Manson et al. .................... 128/142.7 |
| 2,435,167 | 1/1948 | Stetson ............................. 128/142.7 |
| 2,631,287 | 3/1953 | Malcom, Jr. ...................... 128/142.7 |
| 2,642,574 | 6/1953 | Eloranta ................................. 2/436 |
| 2,665,686 | 1/1954 | Wood et al. ............................. 2/435 |
| 2,799,862 | 7/1957 | Rowe ..................................... 2/427 |
| 3,454,864 | 8/1969 | Austin et al. ...................... 128/142.7 |
| 3,818,510 | 6/1974 | Romann ................................. 2/436 |

*Primary Examiner*—Doris L. Troutman
*Attorney, Agent, or Firm*—Burton & Dorr

[57] ABSTRACT

A fog free ski mask including protective covering material form fitting to the head, the neck, and partial shoulder area of the user, goggles affixed to the material and adapted to fit over corrective lenses of a user, and a breathing apparatus for delivering warm air from a remote area of the body and for delivering exhaled moist and warm air from the body to that remote area. The breathing apparatus of the present invention uses a triangular shaped cup form-fitted over the nose and mouth of the user and fitted snugly to the face of the user by means of a strap connected around the rear neck area of the user. Two detachable tubes are connected to the cup on opposing sides and are of sufficient length to drape around each shoulder or to the front of the user to deliver and receive air from a remote area of the user. The cup, tubes, and strap are disposed underneath the protective material and fit firmly against the face.

7 Claims, 5 Drawing Figures

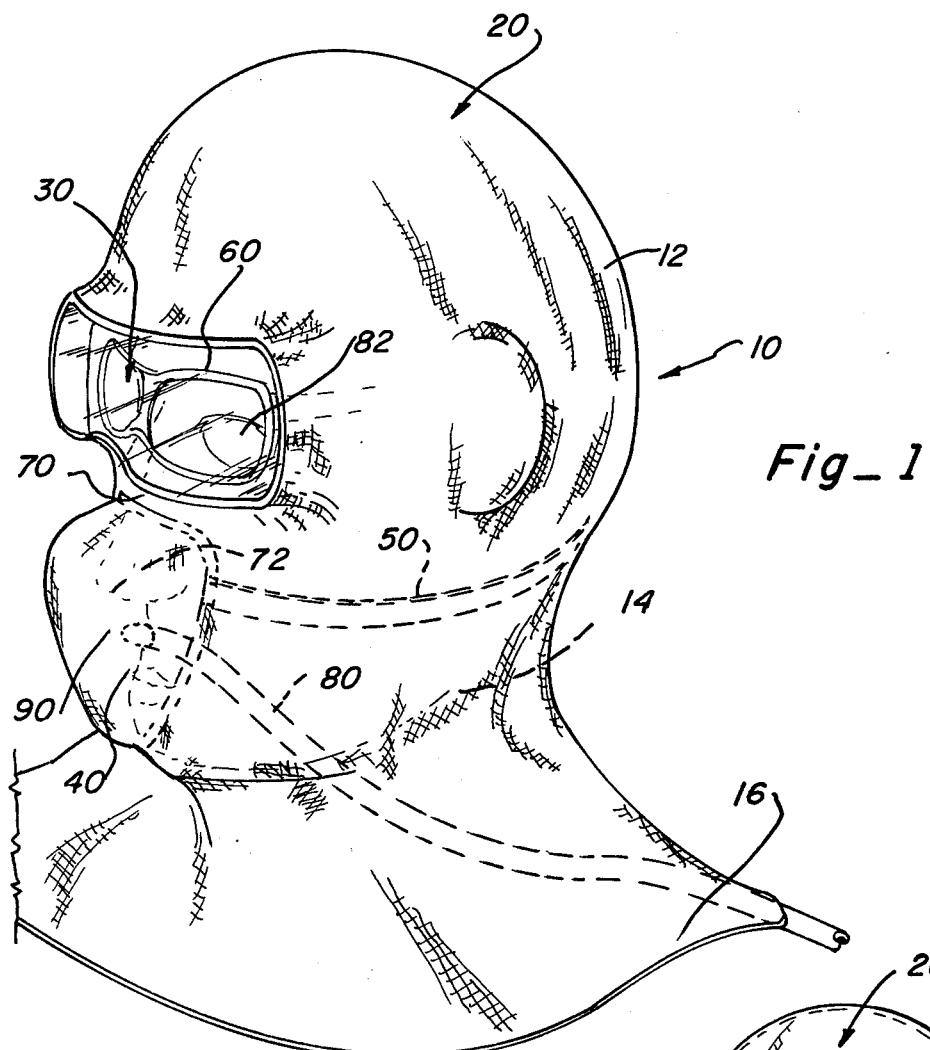
Fig_1
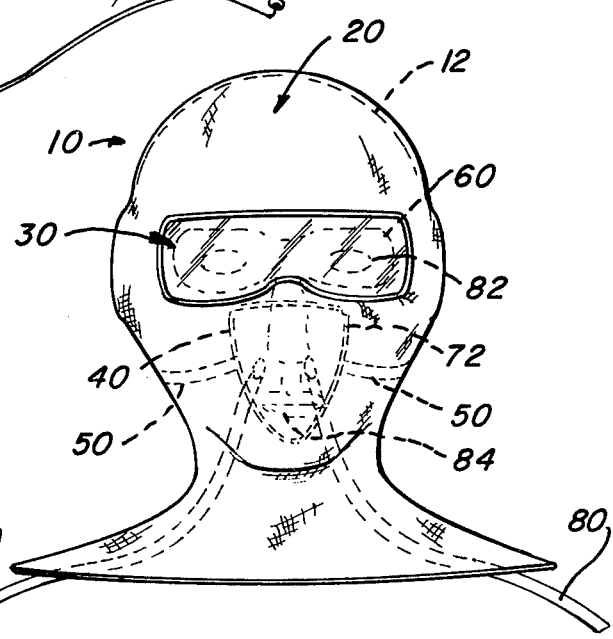
Fig_2

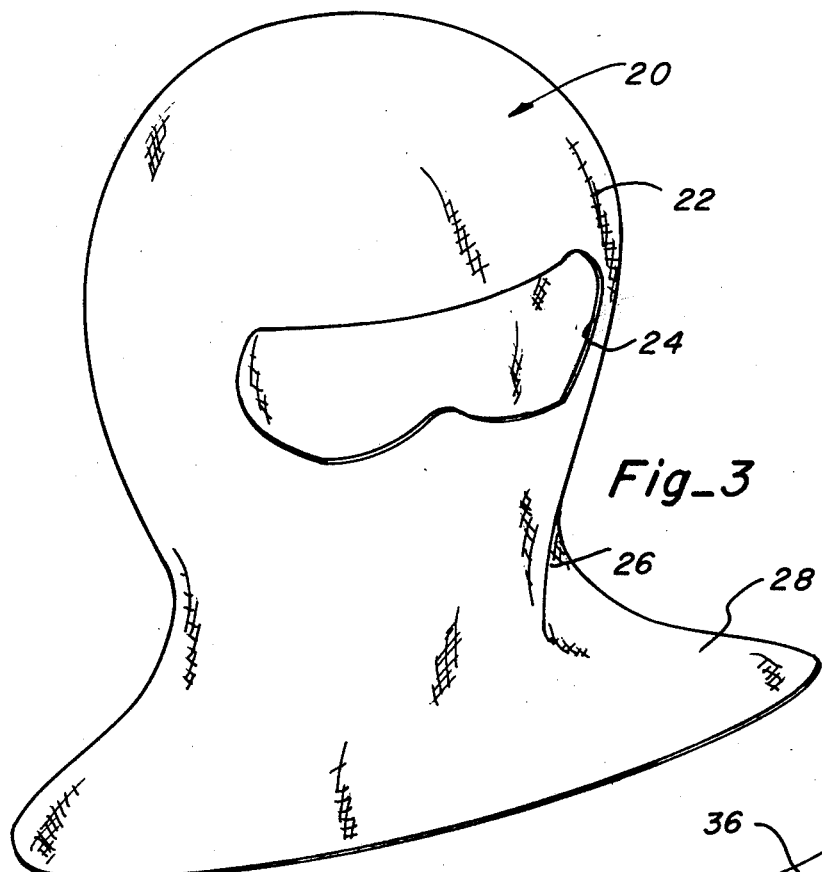
Fig_3
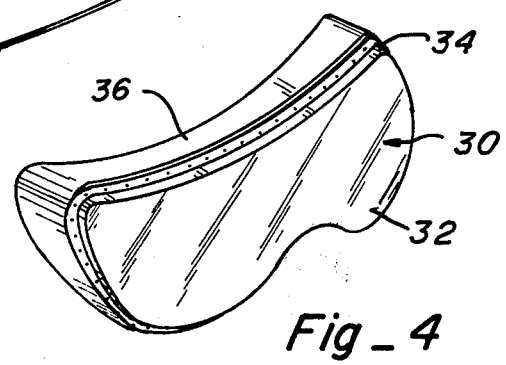
Fig_4
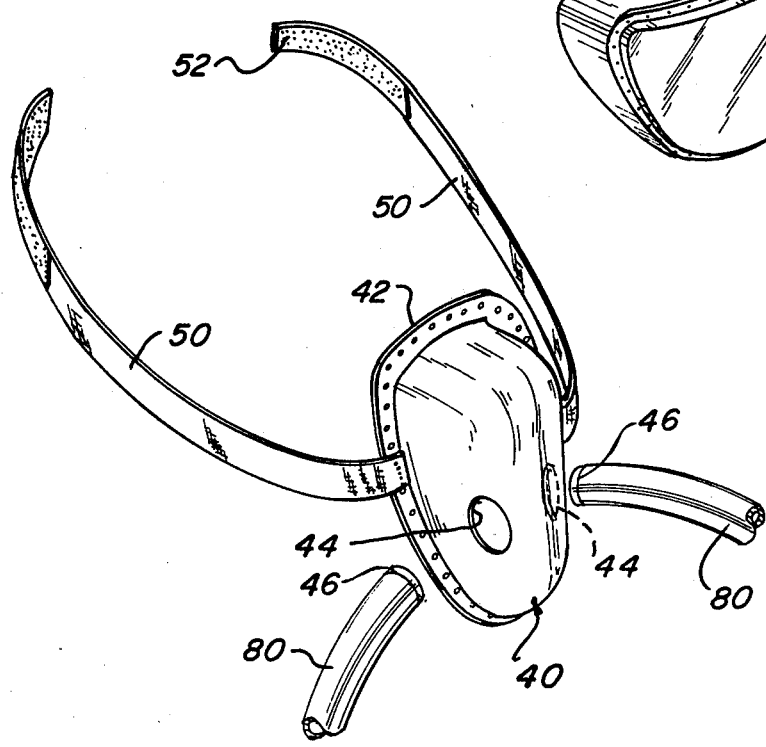
Fig_5

FOG FREE SKI MASK

FIELD OF THE INVENTION

The present invention relates to an apparatus for protecting the head and neck of the user from cold, for preventing fog buildup around the goggles and for delivering heated air to the nose and mouth of the user.

BACKGROUND OF THE INVENTION

The Inventor, prior to applying for this Letters Patent, caused to be conducted a patentability investigation which generated the following prior patented approaches:

| Inventor | U.S. Pat. No. | Date |
| --- | --- | --- |
| Maggi | 2,344,920 | March 21, 1944 |
| Wood et al. | 2,665,686 | Jan. 12, 1954 |
| Wood et al. | 2,667,161 | Jan. 26, 1954 |
| Romann | 3,818,510 | June 25, 1974 |
| McGee et al. | 3,945,044 | March 23, 1976 |

The patent issued to Romann on June 25, 1974, as U.S. Pat. No. 3,818,510 teaches the use of a frost-free face and head enclosure which is designed to maintain a substantially frost-free condition for enhanced visibility by the user. Specifically, by reference to FIG. 1, Romann's "safety helmet" discloses the use of an isolating chamber 18 which contains a check valve 22 and hoses 26 which cooperate with the breathing of the user to expell hot, moist air from the environment around the face mask 12.

The patent issued to Maggi on Mar. 21, 1944, as U.S. Pat. No. 2,344,920 which does not have full head coverage, teaches the use of exit tube 24 to remove exhaled air from the region of the face to the area of the clothing of the wearer or into the hood at the back of the head. Maggi also provides a discharge valve 28.

The patents issued to Wood, et al, U.S. Pat. Nos. 2,665,686 and 2,667,161 disclose similar face masks specifically designed for reducing the temperature of cold being inhaled. The Scott patent teaches the use of a goggle frame specifically designed to include a detachable partial face shield section as shown in FIG. 1.

In essence, the patents issued to Maggi and Romann teach the use of protective masks which remove hot, moist air from the region around the nose and mouth conveyed through tubes to a remote region near the body of the user. However, neither Maggi or Romann teach the use of a fog or frost eliminator specifically designed for ski use. Furthermore, none of the above prior art approaches teach the use of a protective covering form fitted around the head, the neck and partial shoulder area of the user for protection from the cold and to accommodate heating of air in tubes before inhaling. In addition, the present invention contemplates using a flexible protective material so that the user can easily move or orient his head from one angular position to another rapidly and quickly. Furthermore, none of the above prior art approaches teach the use of a protective lens mounted in such a protective covering that is adapted to fit over corrective glasses of a user. Additionally, none of the above prior art approaches teach the use of a separate strap attached to the nose and mouth cup for firmly securing said cup into position. Furthermore, the present invention as hereinafter described, does not use any moving parts which can freeze-up or otherwise malfunction. This is necessary since the user, as he skis, as mentioned, twists his neck from side to side rapidly. By using a separate restraining strap for the cup, virtually no moist warm air from the nose and mouth area is delivered upwardly into the goggle area. It is believed that these comprise major advantages over the above prior patented approaches in that the present invention is specifically designed to be adapted for skiing use and its particular problems associated therewith.

DESCRIPTION OF THE DRAWINGS

FIG. 1 is a perspective side view of the ski mask of the present invention fitted over the head of a user.

FIG. 2 is a front view of the ski mask of the present invention fitted over the head of a user.

FIG. 3 is a perspective view of the protective covering material.

FIG. 4 is a perspective view of the protective goggles of the present invention.

FIG. 5 is a perspective view of the breathing apparatus of the present invention.

OBJECTS OF THE INVENTION

It is an object of the present invention to provide a new and improved ski mask which substantially eliminates fogging of the goggles in use.

It is another object of the present invention to provide a new and improved ski mask which includes protective covering material encompassing the head, neck, and partial shoulder area of the user.

It is another object of the present invention to provide a new and improved ski mask having a breathing apparatus for delivering warmed air to and from a region remote from the nose and mouth of the user.

It is another object of the present invention to provide a new and improved ski mask in which a breathing apparatus is firmly abutted to the face of the user by means of a restraining strap.

It is another object of the present invention to provide a new and improved ski mask in which a cup is placed over the nose and mouth of the user to define an air space above the nose and below the cup which is independent from the air space defined between the goggles and the eyes of the user so that no fluid communication exists between the two air spaces.

It is another object of the present invention to provide a new and improved ski mask having all of the above features or any combination thereof.

Other objects, advantages and capabilities of the present invention will become more apparent as the description proceeds taken in conjunction with the accompanying drawings.

SUMMARY OF THE INVENTION

The present invention includes a protective outer covering form fitting around the head, the neck, and partial shoulder area of the user, a goggles affixed to a preshaped slot of the protective material and designed to fit over the corrective glasses of a user, a breathing apparatus fitting over the nose of the user and disposed and attached on the interior of the protective covering so that it is not visible from the exterior surface.

The protective covering of the ski mask is designed of sufficiently flexible material so that it may be fitted over the top of the head of the user and the neck portion being expandable to fit over the head and contractible to fit snuggly around the neck area when in position.

When the covering is rubberized, wind resistance for ski race situations is greatly reduced.

The goggles are suitably made and designed to bulge outwardly so that corrective glasses of a user are received and so that the goggles do not interfere with such use by the user. The goggles are affixed to a preformed slot in the protective material.

The breathing apparatus comprises a triangular shaped inverted cup designed to fit over only the nose and mouth and attached to the protective material, as well as an outwardly extending flange which conforms to the surface of the face around the nose and mouth. Adjustable straps are attached on opposing sides of the cup and are disposed around the back of the neck area of the user and firmly attached together by means of Velcro or the like. The use of such straps provide snug fitting engagement of the cup to the surface of the face. Also connected to the cup on opposing edges are two downwardly extending tubes which are disposed on either side of the shoulder into the back or front area of the user. The cup cooperates with the face of the user to define an air space disposed therebetween and air can be delivered from the back or front of the user to and from the defined air space.

DESCRIPTION OF THE PREFERRED EMBODIMENT

The ski mask 10 of the present invention is shown in FIG. 1 to totally envelope the head 12, the neck 14, and a portion of the shoulders 16 of the person wearing the ski mask 10. The ski mask 10 includes the material covering 20, a goggle portion 30, and a breathing cup portion 40. The breathing cup 40 is firmly attached by means of a connecting strap 50 around the back of the neck 14 as will be discussed in the ensuing.

The protective covering material 20, as shown in FIG. 1, completely envelopes the head 12, the neck 14, and the upper portion of the shoulders 16 in a flexible, but tight fitting or snug fashion. Accordingly, material 20 can be made of any of a number of conventional knit-like substances of which numerous ski hats and the like are being currently manufactured from. For racing purposes, a rubberized substance to reduce wind resistance may be used. The material 20 tightly fits about the neck 14 to provide a seal therearound and to prevent cold air from entering around the neck area as conventionally occurs and to warm oxygen before inhaling. Current ski mask approaches do not offer any covering of the area around the neck and upper shoulder portions. Therefore, it is not surprising, to expect a large influx of cold air through the neck area of the user not only to his head but also to his body proper. Conventionally, this problem is alleviated by use of scarves or the like. A significant percentage of body heat loss occurs through the head. The insulating effect of the mask reduces this heat loss, thereby conserving energy.

The goggles 30 are affixed to the material 20 along a specially designed cutout in the shape of the goggles. The goggles 30 are preferably designed to be of a raised configuration so that the goggles 30 can fit over any corrective lens 60 of the user. The cup breathing apparatus 40 is also affixed by sewing or gluing under the material 20 and creates an air space 90 between the cup 40 and the nose 72. Air is delivered to this air space 90 by means of a tube 80 which is disposed from the air space 90 rearwardly or forwardly over the shoulder 16 of the user. In this manner, heated air from the back or front regions of the user which are covered by coats or the like, is delivered rapidly and readily into the nose and mouth of the user for breathing. The air space 90 between the eyes 82 of the user and the goggles 30 is not in fluid communication with the air space 90. This lack of communication between the two air spaces 90 and 70 is primarily due to the cooperation of the cup 40 being held firmly against the regions around the nose by a strap 50.

The ski mask 10 of the present invention as shown in FIG. 1, therefore, provides full protective coverage around the total area of the head 12 and the neck 14. Such protection, for example, is important for ski patrol members who for long periods of time must be out searching for victims of a skiing accident or avalanche. Such complete protective covering also finds application in snowmobile uses where due to the velocity of the snowmobile, certain parts of the head 12 and the neck 14 can be frost bitten quickly due to the severe wind chill conditions. In applications such as snowmobiles, the material 20 can be appropriately manufactured from such cold protective material as insulated leather or the like.

The ski mask 10 of the present invention provides goggles 30 which are adapted to fit with ease and convenience over corrective lenses 60 without the use of a strap or the like connected to the goggles 30. The material 20 is connected to the goggles 30 around the periphery of the goggles and serves to snugly and firmly position the goggles over the corrective lenses 60 without interfering with the protective lens or the stem (not shown) of the lens thereof.

The ski mask 10 of the present invention further provides the delivery of heated air from remote regions of the body such as the area behind or in front of the shoulders 16. Therefore, the user can easily wear the ski mask 10 of the present invention and be able to breathe and exhale warm air. By providing a cup 40 over the nose and mouth, the exhaled moist and heated air is delivered through a remote region separate and apart from the air space 70 between the goggles 30 and the eyes 82. Therefore, there is no possibility of the goggles 30 or, if used, the corrective lens 60 from fogging up. This is an important improvement over prior and conventional approaches especially for the users of corrective lenses. On exceedingly cold days, for the first time, members of the ski patrol can obtain full facial covering without the worry of goggles or lens fogging. Furthermore, snowmobile users can obtain full protective neck and facial and head coverage without the worry of their vision being impaired by fogging.

As will be brought out in greater detail in the ensuing discussion, all of the various components of the present invention are flexible including the cup 40 and the goggles 30. Thus, in the event of an accident such as falling down the slope or a snowmobile accident, the user of the ski mask 10 of the present invention need not worry about gouging his head with cutting edges or the like. In fact, due to the specific construction of the present invention, the goggles 30 and cup 40 provide protective coverings over vital organs of the body.

FIG. 2 illustrates the front view of the ski mask 10 of the present invention and shows the placement of the breathing cup 40 over the nose 72 and below the lips 84. Furthermore, the orientation of the goggles 30 over the corrective lens 60 is also shown. Due to the sweep-around nature of the goggles 30, greater peripheral vision is obtainable with the ski mask 10 of the present invention than heretofore offered. This is especially true for wearers of corrective lenses. Additionally, it is to be noted, as shown in FIG. 2, that two delivery tubes 80 are provided for delivering air from a region behind or in front of each shoulder 16.

The covering material 20 is shown in FIG. 3 to include a top dome portion 22 which is spherically shaped to fit snugly over a person's head. The covering material 20 has formed therein a cutout 24 substantially in the shape of the goggles 30. Below the spherical or dome portion 22 is the neck region 26. The neck region 26 has a circumference corresponding substantially to that of the neck of the user. Of course, the neck region 26 has sufficient expansion so that the user may stretch the neck region of the material 20 over his head and downwardly over the nose and mouth. When in position over the neck, however, the neck region 26 contracts or constricts to the shape of the neck but not so to be unduly uncomfortable by the user (children and adults alike). Continuous with the neck region 26 is a shoulder region 28 which lays loosely onto the shoulders in the vicinity of the neck. It is to be expressly understood that the covering material 20 can be conventionally manufactured into the shape shown in FIG. 3 and of such material to allow easy access of the material to the head and neck and removal therefrom. Furthermore, it is to be expressly understood that any one of a number of conventional approaches can be used to construct the covering material 20 in the shape as shown in FIG. 3. For instance, this might be a one-piece knit construction, or it may be made from two pieces conveniently sewn together.

In FIG. 4 is shown the goggles 30 of the present invention to include the lens portion 32 and a connecting flange portion 34. The covering material 20 along the periphery of the cutout 24 is designed so that the periphery of the cutout 24 abuts the lens portion 32 with the flange portion 34 underlying a comparable region of the cutout 24. By means of conventional sewing and adhering techniques, the flange 34 or area 36 is affixed to the periphery of cutout 24. The lens portion 32 of the goggles 30 may be designed to bulge outwardly to accommodate the corrective lenses of the user and may be made of thermopane material.

In FIG. 5 are shown the details of the device for delivering air from a remote region of the body to the space around the nose and mouth of the user. This apparatus includes the cup 40 which is designed substantially triangular in shape being of greater width in the region near the upper portion of the nose and tapering to a narrower width in the region below the mouth. The cup 40 is shaped to provide an air space 90 between the interior of the cup 40 and the exterior surface of the nose 72. A flange 42 extends around the periphery of the cup 40 and is the vehicle by means of which the cup 40 is attached to the covering material 20. It is to be noted that no cutout is provided for the nose cup as is provided for the goggles 30. The cup 40 is disposed on the interior surface of the covering material 20 and the covering material 20 is sewn to the flange 42 in a conventional fashion. Therefore, when constructed, the cup is covered by the protective material 20 to provide insulation against cold air. This prevents frost buildup from the warm air exhaled through the nose onto the interior surface of the cup. Furthermore, by attaching the cup to the interior surface of the covering material 20, a more aesthetic appearance is obtained. Adjustable straps 50 are provided on opposing ends of the cup 40 and are designed to be attached around the back of the neck portion of the user by means of Velcro fastening 52 or the like. In this fashion, the straps 50 cause the cup 40 to be snugly positioned against the surface of the skin in the area around the nose and by use of the flange regions 42, substantially an air tight seal is created. Air is delivered into the air space 70 by means of hollow tubes 80 which are connected to opposing sides of the cup 40 in formed holes 44. The tubes 80 can be conventionally interconnected to the formed holes 44. The tubes 80 are sufficient length so that each of the tubes may be draped off the shoulder to a remote region to the back or front of the user. The tubes have a slight groove 46 at the end so as to allow a snap in - snap out effect for efficient cleaning. The groove 46 occurs 1/4 inch from the end of the air tubes 80 so as not to interfere with the nose.

Although the present invention has been described with a certain degree of particularity, it is understood that the present disclosure has been made by way of example and that changes in details of structure may be made without departing from the spirit thereof.

I claim:

1. A fog-free ski mask for covering the head of a skier, said apparatus comprising:

form fitting flexible material encircling and covering the head, neck and partial shoulder area of said person, the material around said neck area being capable of stretching over said head and snugly constricting around said neck, said material having a formed slot located at the eyes of said person, goggles attached to said material around the periphery of said slot, means covering the nose and mouth of said person and attached to the inside surface of said material for delivering and removing air from said nose and mouth from and to a region below the neck area, said delivering means being capable in conjunction with the body heat of said skier of pre-warming said delivered air, and means connected to said delivering and removing means for firmly holding said delivering and removing means to a region of said face around said nose and mouth, said holding means being disposed between the inside surface of said material and the outer surface of said head.

2. The ski mask of claim 1 in which said delivering and removing means comprises:

a cup attached to the inside surface of said material, said cup being shaped to rigidly extend over said nose and mouth and to define an air space between said nose and mouth and the interior of said cup, and one or a plurality of tubes connected to said cup for providing air communication between said air space and said region below the neck area.

3. The ski mask of claim 2 further comprising first and second straps connected to opposing ends of said cup for encircling said head, said straps being capable of interconnecting with each other to firmly hold said cup to said head.

4. The ski mask of claim 2 in which each of said tubes is selectively releasable from said cup.

5. The ski mask of claim 2 wherein each of said tubes has a groove formed in one end for selectively engaging said cup.

6. The ski mask of claim 2 in which said cup further comprises a flange extending around the periphery of said cup, said flange being oriented to firmly abut the surface of said face and said material being connected to said flange.

7. A ski mask comprising:
- form fitting flexible material encircling and covering the head, neck and partial shoulder area of said person, the material around said neck area being capable of stretching over said head and constricting around said neck, said material having a formed slot located at the eyes of said person,
- goggles attached to said material around the periphery of said slot,
- a cup attached to the inside surface of said material, said cup being shaped to rigidly extend over said nose and mouth and to define an air space between said nose and mouth and the interior of said cup, said cup further comprising a flange extending around the periphery of said cup, said flange being oriented to snugly abut the surface of said face and said material being connected to said flange,
- one or a plurality of detachable tubes connected to said cup for providing air communication between said air space and a remote region near said person's body, and
- first and second straps connected to opposing ends of said cup for encircling said head, said straps being capable of interconnecting with each other to firmly hold said cup to said head and being disposed between the inside surface of said material and the outer surface of said head.

* * * * *